United States Patent [19]

Russell

[11] Patent Number: 6,027,713
[45] Date of Patent: Feb. 22, 2000

[54] COMPOSITION AND METHOD FOR THE TREATMENT OF EXERCISE INDUCED PULMONARY HEMORRHAGE

[75] Inventor: Charm Russell, Des Moines, Iowa

[73] Assignee: Meri Charmyne Russell, Des Moines, Iowa

[21] Appl. No.: 08/976,186

[22] Filed: Mar. 6, 1997

[51] Int. Cl.[7] .................... A61L 2/22; A61L 9/04
[52] U.S. Cl. ................ 424/45; 514/565; 514/929; 514/958
[58] Field of Search ............ 424/45; 514/958, 514/929, 565

[56] References Cited

U.S. PATENT DOCUMENTS

| | | | |
|---|---|---|---|
| 5,232,928 | 8/1993 | Skiles | 514/291 |
| 5,485,827 | 1/1996 | Zapol et al. | 128/200 |
| 5,570,683 | 11/1996 | Zapol | 128/200.14 |
| 5,718,892 | 2/1998 | Keefer et al. | 424/78.27 |

OTHER PUBLICATIONS

Euine Vet Sep. 19, 1997(5):428–34, "Exercise–induced pulmonary haemorrhage in the horse: results of a detailed clinical, post mortem and imaging study. VIII. Conclusions and implications", by M.W. O'Callaghan et al.

Equine Vet J Nov. 26, 1994 (6):482–5, "A survey of exercise–induced pulmonary haemorrhage in Quebec standardbred racehorses", by J.M. Lapointe et al.

Vet Rec Sep 15, 1984 ;115(11):268–9, "Effect of bedding on the incidence of exercise induced pulmonary haemorrhage in racehorses in Hong Kong", by D.K. Mason et al.

Can J Vet Res Apr. 1991 ;55(2):101–6, "Hemostatic studies in racing standardbred horses with exercise–induced pulmonary hemorrhage. Hemostatic parameters at rest and after moderate exercise", by I.B. Johnstone et al.

Res Vet Sci May 1986;40(3):406–7, "Sex variation in the prevalence of exercise–induced pulmonary haemorrhage in racing quarter horses", by C.J. Hillidge et al.

Equine Vet. J. Suppl Jun. 1990 (9):47–52, "Pulmonary artery, aortic and oesophageal pressure changes during high intensity treadmill exercise in the horse: a possible relation to exercise–induced pulmonary haemorrhage", by B.K. Erickson et al.

Equine Vet J Jan 1994.; 26 (1):51–4, "Frusemide attenuates the excercise–induced rise in pulmonary capillary blood pressure in horses", by M. Manohar et al.

Am J Vet Res May 1981; 42(5):703–7, "Exercise–induced pulmonary hemmorrhage in exercising Throughbreds: preliminary study", by J. R. Pascoe et al.

Cornell Vet Jul 1984; 74(3):263–8, "Exercise–induced pulmonary hemmorrhage in exercising Thoroughbreds: preliminary results with pre–exercise medication", by C.R. Sweeney et al.

J Vet Intern Med Jul.–Aug. 1991 ;5(4):211–8, "Pharmacology of furosemide in the horse: a review", by K.W. Hinchcliff et al.

Equine Vet J May 1995; 17(3):166–72, "Review of exercise induced pulmonary haemorrhage and its possible relationship with mechanical stress", by A.F. Clarke.

*Primary Examiner*—Thurman K. Page
*Assistant Examiner*—Lakshmi Channavajjale
*Attorney, Agent, or Firm*—Gilberto M. Villacorta; Pepper Hamilton LLP

[57] ABSTRACT

A composition for the treatment of exercise induced pulmonary hemorrhage, particularly in horses. The composition comprises arginine and is formulated for inhalation. The invention includes an inhaler apparatus specially adapted for the administration of the composition.

14 Claims, 1 Drawing Sheet

COMPOSITION AND METHOD FOR THE TREATMENT OF EXERCISE INDUCED PULMONARY HEMORRHAGE

TECHNICAL FIELD

The present invention relates to a composition for the treatment of exercise induced pulmonary hemorrhage, particularly in horses. The composition comprises arginine and is formulated for inhalation. The invention also includes an inhaler apparatus specially adapted for the administration of the composition.

BACKGROUND ART

It has been demonstrated that pulmonary capillary blood pressure of strenuously exercising horses increases dramatically. Therefore, alveolar-capillary blood-gas barrier, which has to be extremely thin to provide for passive diffusion of $O_2$, is exposed to high transmural pressures resulting in its stress failure and the ensuing exercise induced pulmonary hemorrhage (EIPH). The rapid rate of rise in pulmonary capillary blood pressure of Thoroughbreds upon rapid acceleration is probably another factor which contributes to onset of EIPH very early in the course of a race. Logically, in the context of preventing EIPH, the pulmonary blood-gas barrier therefore needs to be strengthened and or the pulmonary vascular pressures of racing Thoroughbreds be lower. Whereas the former may require genetic manipulation (thickness of pulmonary blood-gas barrier must not increase however, because of impediment to gas exchange), the latter may be accomplished with selective pulmonary vasodilator agents. It is known that pre-exercise administration of fursemide attenuates significantly the exercise induced rise in pulmonary vascular pressures of horses.

At sea level, in resting animals and man, pulmonary vascular pressures are about ¼ to ⅓ of those in the systemic circulation because pulmonary vascular resistance is kept at a very low level; in standing horses pulmonary vascular resistance is only ⅒th of the systemic vascular resistance. It has been suggested (Griffith et al. 1987; Ignarro 1989) that pulmonary vascular bed of normoxic resting animals is kept in a dilated state by the tonic release of nitric oxide (NO; also known as endothelium derived relaxing factor of EDRF). Experiments in several species (cat, rabbit, guinea pig and lamb) have demonstrated that inhibition of the NO synthesis increase basal tone in pulmonary vascular bed. It has been demonstrated that NO inhalation reversed pulmonary vasoconstriction induced by alveolar hypoxia in adult sheep. The pulmonary vasodilator effect of exogenously administered acetylcholine is believed to be mediated via release of NO (Ignarro 1989). Increased blood velocity/shear rate is also known to promote release of NO from the vascular endothelium (Griffith et al. 1987; Cooke et al. 1990; Griffith and Edwards 1990). The vascular smooth muscle relaxant action of nitrovasodilators such as amyl nitrate, glyceryl trinitrate (nitroglycerin) and nitroprusside, is via activation of soluble guanylate cyclase, which elevates the intracellular cyclic GMP level (Ignarro 1989).

A gaseous nitric oxide-donor treatment of vasoconstriction is known. U.S. Pat. No. 5,480,869 discloses anti-inflammatory peptide analogs and their use as a treatment for inhibiting vascular leakage in injured tissues, including damaged lungs tissue. Several peptides in this patent include arginine, but the patent does not suggest using the amino acid L-arginine independently. The patent discloses intravenous, intradermal and subcutaneous administration, but makes no suggestion of any gaseous applications of the peptide analogs.

U.S. Pat. No. 5,485,827 discloses methods and devices for treating pulmonary vasoconstriction and asthma. The patent indicates that a mammal at risk of developing pulmonary vasoconstriction may be treated with a therapeutically effective amount of a nitric oxide-releasing compound. Also disclosed is a portable inhaler that could be used to administer inhalation therapy for pulmonary vasoconstriction.

"Effects Of Glyceryl Trinitrate (Nitroglycerine) On Pulmonary Vascular Pressures In Standing Thoroughbred Horses", Manohar, M, *Equine Vet. J.*, (July, 1995) 27(4):275–80; discloses using nitroglycerine to lower the blood pressure of thoroughbred horses and allegedly prevent exercise-induced pulmonary hemorrhaging. The article concentrates on the use of nitroglycerine and not on the use of L-arginine.

There is a need in the art for alternative treatments for EIPH. The present invention overcomes the deficiencies of the prior art by providing a composition and an inhaler apparatus for the treatment of EIPH.

DISCLOSURE OF THE INVENTION

It is an object of the invention to provide a method of alleviating the negative effects of exercise-induced pulmonary hemorrhage in mammals comprising administering through inhalation an effective amount of arginine.

It is another object of the invention to provide an inhaler apparatus for administration of a composition for the treatment or prevention of exercise-induced pulmonary hemorrhage in animals in the form of a gas mask or inhaler.

The above and other objects of the invention will become readily apparent to those of skill in the relevant art from the following detailed description and figures, wherein only the preferred embodiments of the invention are shown and described, simply by way of illustration of the best mode of carrying out the invention. As is readily recognized the invention is capable of modifications within the skill of the relevant art without departing from the spirit and scope of the invention.

DESCRIPTION OF THE INVENTION

Figure 1:
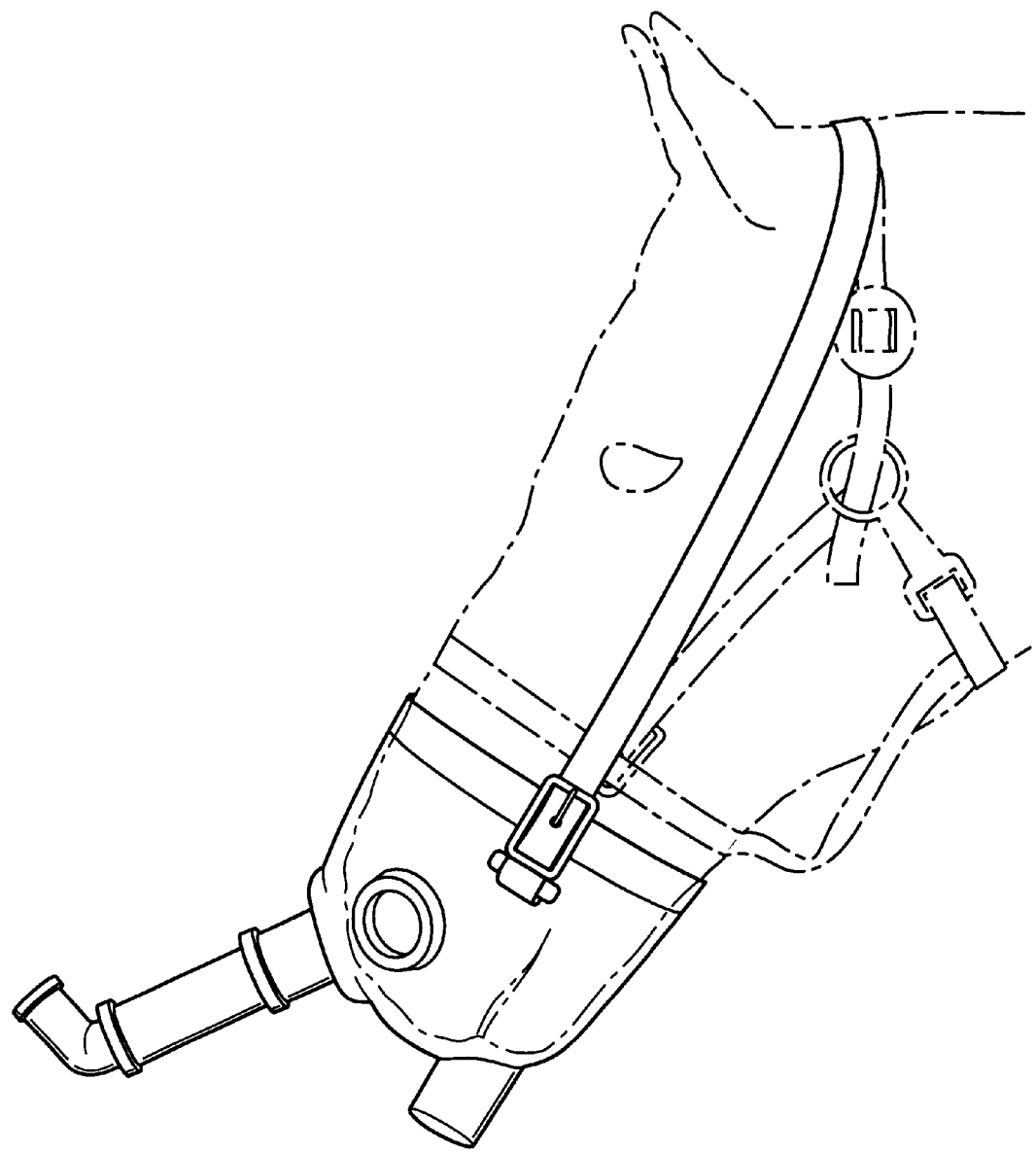
FIG. 1 depicts an embodiment of the gas mask/inhaler of the invention.

Exercise-induced pulmonary hemorrhage (EIPH) is defined as bleeding from the lungs as a consequence of exertion. Most horses involved in competitive racing experience EIPH. The incidence of EIPH ranges from about 30% for Standardbreds and polo ponies to >60% for Thoroughbreds, Quarterhorses and Appaloosas. The minimum level of exertion needed to induce EIPH is unknown. Though it has been observed in some Thoroughbred horses after trotting, cantering and slow training gallops, it generally is associated with more strenuous exertion, such as competitive flat racing, pacing, trotting, jumping or barrel racing.

The present invention provides an arginine composition to be administered to an animal to alleviating the negative effects of exercise-induced pulmonary hemorrhage. An appropriate dosage may be calculated to alleviating the negative effects of exercise-induced pulmonary hemorrhage. In a preferred embodiment the dosage is 15–30 ml per 454 kg of body weight of the animal to which the arginine is administered. Preferred administration is twice daily.

The arginine compound is useful in pharmaceutical compositions (wt %) of the active ingredient with a carrier or vehicle in the composition in about 0.01 to 99%, preferably 1 to 20% and more preferred, about 1 to 3%.

The following are several formulations for preferred embodiments of the arginine inhalation solution of the present invention.

| Example 1 | | | |
|---|---|---|---|
| L-Arginine | | 1.6% | |
| Na-Benzoate | | 500 | mg |
| NaCl 0.9% | qs | 240 | ml |
| Example 2 | | | |
| L-Arginine | | 40.8 | g |
| NaBenzoate | | 500 | mg |
| NaCl 0.9% | qs | 240 | ml |
| Example 3 | | | |
| L-Arginine | | 163.2% | |
| NaBenzoate | | 500 | mg |
| NaCl 0.9% | | 240 | ml |
| Example 4 | | | |
| L-Arginine | | 122.4 | G |
| NaBenzoate | | 500 | mg |
| NaCl 0.9% | qs | 240 | ml |

These are sterile solutions for use in an aerosol mask or inhaler in accordance with the present invention.

The preferred dose is 15–30 ml twice daily for the Example 1 formulation which is the preferred formulation.

Preferably the arginine is L-arginine. It is also preferred that the effective amount of arginine is administered to the lungs of the mammal. It is preferred that the mammal is a horse.

It is most preferred that the arginine is administered as an aerosol, with the aid of a mask or inhaler. In a preferred embodiment the mask or inhaler is adapted to the shape of the head of the animal receiving the arginine.

The effective amount of arginine is effective to cause the dilation of the blood vessels of the mammal's lungs.

Other aerosol formulations may be prepared in accordance with the general aerosol formulations set forth in Remingtons Pharmaceutical Sciences, 18th Ed., Mack Publishing Co. (1990). See Chapter 92, entitled "Aerosols" incorporated herein by reference in its entirety. Aerosol formulations may include propellants, such as hydrocarbon propellants or compressed gas propellants. Compressed gas propellants may be selected from nitrogen, carbon dioxide or nitrous oxide. Hydrocarbon propellants may include and are not limited to butane, propane or isobutane. Liquified gas propellants include fluorinated chlorinated hydrocarbons, hydrochlorofluorocarbons, hydrocarbon ethers, and hydrocarbons. The aerosol formulation may include a solvent such as ethyl alcohol.

The gas mask or inhaler of the invention may provide a metered dose of arginine.

The purpose of the above description and examples is to illustrate some embodiments of the present invention without implying any limitation. It will be apparent to those of skill in the art that various modifications and variations may be made to the composition and method of the present invention without departing from the spirit or scope of the invention. All patents and publications cited herein are incorporated by reference in their entireties.

I claim:

1. A method of treating exercise-induced pulmonary hemorrhage in equines comprising administering through inhalation an effective amount of arginine in a physiologically acceptable carrier.

2. The method of claim 1, wherein said arginine is L-arginine.

3. The method of claim 1, wherein an effective amount of arginine is administered to the lungs of the equine.

4. The method of claim 1, wherein said equine is a horse.

5. The method of claim 1, wherein said carrier comprises a gas.

6. The method of claim 1, wherein said arginine is administered with the aid of an inhaler or mask.

7. The method of claim 6, wherein said inhaler or mask comprises a shape adapted to fit the head of the animal to be administered the arginine.

8. The method of claim 1, wherein the amount of arginine is effective to cause dilation of the blood vessels of the equine's lungs.

9. The method of claim 1, wherein said carrier comprises an ethyl alcohol solvent.

10. The method of claim 1, wherein said arginine is administered with the aid of an atomizer.

11. An inhaler for treating exercise-induced pulmonary hemorrhage in equines comprising an inhaler filled with an effective amount of arginine in a physiologically acceptable carrier, wherein said inhaler is shaped to conform to the shape of the nose of a horse.

12. The inhaler of claim 11, wherein said carrier comprises a gas.

13. A method of treating exercise-induced pulmonary hemorrhage in equines comprising administering through inhalation an effective amount of a composition consisting essentially of arginine in a physiologically acceptable carrier.

14. The method of claim 13, wherein said composition further comprises sodium benzoate and sodium chloride.

* * * * *